United States Patent [19]

Ogawa

[11] Patent Number: 4,806,434

[45] Date of Patent: Feb. 21, 1989

[54] MEDIUM FOR ELECTROPHORESIS

[75] Inventor: Masashi Ogawa, Asaka, Japan

[73] Assignee: Fuji Photo Film Co., Ltd., Kanagawa, Japan

[21] Appl. No.: 752,938

[22] Filed: Jul. 8, 1985

[30] Foreign Application Priority Data

Jul. 6, 1984 [JP] Japan .................................. 59-140915
Jul. 6, 1984 [JP] Japan .................................. 59-140916

[51] Int. Cl.$^4$ ............................................. B32B 27/08
[52] U.S. Cl. ............................... 428/474.4; 204/182.6; 524/28; 524/458; 524/156; 524/215; 524/210; 524/916
[58] Field of Search ................ 525/291; 524/458, 814, 524/817, 916; 204/182.6; 428/474.4

[56] References Cited

U.S. PATENT DOCUMENTS

| 3,351,618 | 11/1967 | Toepfl ................................ 524/814 |
| 3,725,476 | 4/1973 | Blackwood ........................ 525/291 |
| 4,415,428 | 11/1983 | Nochumson ...................... 204/182.8 |
| 4,548,869 | 10/1985 | Ogawa ............................... 204/182.8 |
| 4,548,870 | 10/1985 | Ogawa ............................... 204/182.8 |
| 4,560,710 | 12/1985 | Schulz ................................ 526/287 |
| 4,579,783 | 4/1986 | Ogawa ............................... 204/182.8 |
| 4,582,868 | 4/1986 | Ogawa ............................... 204/182.8 |
| 4,650,848 | 3/1987 | Schulz ................................ 526/287 |

FOREIGN PATENT DOCUMENTS

| 0125763 | 11/1984 | European Pat. Off. ......... 204/182.8 |
| 0137753 | 4/1985 | European Pat. Off. ......... 204/182.8 |
| 0168233 | 1/1986 | European Pat. Off. ............ 525/291 |
| 0195468 | 9/1986 | European Pat. Off. ............ 525/291 |

Primary Examiner—C. Warren Ivy
Attorney, Agent, or Firm—Jules E. Goldberg

[57] ABSTRACT

A medium for electrophoresis comprising an aqueous acrylamide gel formed by crosslinking polymerization of an acrylamide compound and an acrylamide copolymer having at least one specifically selected constitutional repeating unit in the presence of water. The medium may contain a water-soluble polymer and agarose. The medium may contain a modifier such as an anionic surfactant or a compound having at least one carbamoyl group.

10 Claims, No Drawings

MEDIUM FOR ELECTROPHORESIS

BACKGROUND OF THE INVENTION

1. Field of the Invention

This invention relates to a medium for electrophoresis suitably employable for analysis of biopolymers such as proteins, as well as for determination of base sequence of DNA, RNA, their fragments, and their derivatives.

2. Description of Prior Arts

For the analysis of biopolymers such as proteins, or for the determination of base sequence of DNA or RNA, the electrophoresis can be carried out in the following manner.

A membrane medium for electrophoresis prepared by coating or casting a membrane-forming material such as agar, cellulose, cellulose acetate, starch, silica gel or polyacrylamide gel over a support such as a glass plate or a transparent plastic sheet (or film) is impregnated with a buffer solution; on the medium is applied to a substance to be analyzed (sample); the applied sample is developed (or resolved) on or in the medium by applying a voltage between the both ends of the support; the developed substance is dyed thereon; and then the dyed sample is measured on the optical density to quantatively determine the developed components of the sample.

Details of the electrophoresis and medium therefor are given in "Experimental Text for Electrophoresis (5th revision)" editted by Electrophoresis Society of Japan (Bunkodo, 1975), "Modern Electrophoresis" editted by Alki & Nagai (Hirokawa Shoten, 1973), etc.

Recently, the electrophoresis has been frequently employed to analyze substances originating from a living body; for instance, the analyses of proteins originating from a living body are generally performed in the course of biochemical analysis for diagnosis. The determinations of base sequences of DNA or RNA are also performed in the course of the study in the genetic engineering technology.

As the membrane or sheet for electrophoresis, a filter paper was previously employed, but recently an agarose membrane or a polyacrylamide gel membrane (or medium) has been employed from the viewpoints of their advantageous properties. Particularly, the polyacrylamide gel membrane showing a molecular sieve function is widely employed recently. More particularly, in the method for determination of base sequence of DNA, RNA, their fragments, and their derivatives according to the post-label method, a procedure of slab electrophoresis using a polyacrylamide gel membrane has become essential.

The polyacrylamide gel membrane can be prepared by crosslinking polymerization of a monomer such as acrylamide and a two-functional crosslinking agent such as N,N'-methylenebisacrylamide under an oxygen-free condition in the presence of water and a polymerization catalyst. In the course of the preparation of the polyacrylamide gel membrane, a modifier such as an anionic surfactant, urea or formamide is be incorporated into the membrane in certain cases.

Since the polymerization reaction for the preparation of polyacrylamide is a radical crosslinking polymerization as described above, the polymerization can be easily inhibited by the presence of oxygen. Therefore, the gel membrane should be prepared in the absence of oxygen. For this reason, a polyacrylamide gel membrane is generally prepared by a process involving: introducing an aqueous solution (gel-forming solution or gel solution) containing acrylamide, a crosslinking agent and a polymerization catalyst into a cell formed between two glass plates with a certain clearance (e.g., 0.3–1 mm); sealing the gel-forming solution from oxygen; and causing the crosslinking polymerization to prepare the desired gel membrane.

The polyacrylamide gel membrane prepared as above is employed for electrophoresis. For example, the electrophoresis for analysis of biopolymers such as proteins is performed in the manner such as described below.

The prepared polyacrylamide gel is horizontally or vertically placed for performing slab electrophoresis. The electrophoresis is performed for a certain period of time under predetermined conditions, and the desired analysis of the components originating from the living body is done after dyeing the electrophoresed gel membrane with, for instance, Ponceau 3R (Ciba-Geigy), Coomassie Brilliant Blue G-250 (ICI), or silver.

Since the study in the genetic engineering technology has advanced recently, quick determination of the base sequence of DNA, etc. is highly desired. The polyacrylamide gel membrane prepared as above is also used for electrophoresis for determination of base sequence of DNA in the manner such as described below.

The polyacrylamide gel membrane is vertically placed in the form of being sandwiched between the glass plates, and in the first place a pre-electrophoresis procedure is carried out. Then, a certain amount of a sample (e.g., $^{32}$P-labeled DNA cleaved by Maxam-Gilbert method) is introduced into sample slots provided on the membrane, and electrophosis is carried out. After the electrophoresis is carried out for a certain period of time (e.g., approx. 6–12 hours), one glass plate is removed carefully. Then, the exposed gel membrane is covered with a polymer film such as a poly(vinylidene chloride) film and subjected to the autoradiographic process. The autoradiographic process is carried out by the following procedures: A radiographic film and an intensifying screen are superposed successively on the film covering the gel membrane, whereby exposing the radiographic film to the gel membrane at a low temperature (e.g., −80° C.) for a certain period of time (e.g., approx. 10–20 hours). After the exposing procedure, the radiographic film is developed, and the resolved pattern reproduced on the film is studied for determination of the base sequence of DNA, etc.

SUMMARY OF THE INVENTION

An object of the present invention is to provide a medium for electrophoresis which is suitably employable for analysis of biopolymers such as proteins or DNA.

Another object of the invention is to provide a medium for electorphoresis which has high resolving power as well as improved processibility.

A further object of the invention is to provide a lightweight and tough medium for electrophoresis.

There is provided by the present invention a medium for electrophoresis comprising an aqueous acrylamide gel formed by crosslinking polymerization of an acrylamide compound and an acrylamide copolymer in the presence of water, said acrylamide copolymer having at least one constitutional repeating unit selected from the group consisting of:

(1) a repeating unit having the formula (1):

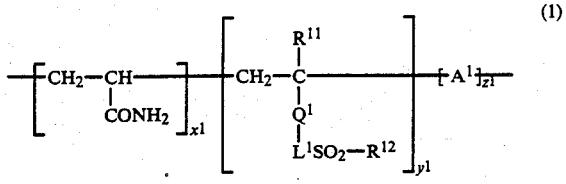

in which $R^{11}$ is the hydrogen atom or an alkyl group containing 1–6 carbon atoms; $Q^1$ is —COO—, —CON($R^{11}$)—, or an arylene group containing 6–10 carbon atoms; $L^1$ is a divalent group containing at least one linkage selected from the group consisting of —COO— and —CON($R^{11}$)— and containing 3–15 carbon atoms, or a divalent group containing at least one linkage selected from the group consisting of —O—, —N($R^{11}$)—, —CO—, —SO—, —SO$_2$—, —SO$_3$—, —SO$_2$N($R^{11}$)—, —N($R^{11}$)CON($R^{11}$)— and —N($R^{11}$)COO—, and containing 1–12 carbon atoms, in which $R^{11}$ has the same meaning as defined above; $R^{12}$ is —CH=CH$_2$ or —CH$_2$CH$_2$X$^1$, in which X$^1$ is a substituent replaceable with a nucleophilic group or releasable in the form of HX$^1$ by a base; $A^1$ is a divalent group derived from an ethylenic unsaturated monomer copolymerizable with monomers forming other unit portions; and $x^1$ and $y^1$ both representing molar percents range from 50 to 99, and from 1 to 50, respectively, and $z^1$ represents the remaining molar percent including O; and (2) a repeating unit having the formula (2):

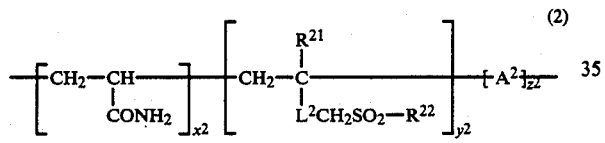

in which $R^{21}$ is the hydrogen atom or an alkyl group containing 1–6 carbon atoms; $R^{22}$ is —CH=CH$_2$ or —CH$_2$CH$_2$X$^2$, in which X$^2$ is a substituent replaceable with a nucleophilic group or releasable in the form of HX$^2$ by a base; $L^2$ is a divalent group selected from the group consisting of an alkylene group containing 1–6 carbon atoms, an arylene group containing 6–12 carbon atoms, —COZ$^2$—, and —COZ$^2$R$^{23}$—, in which R$^{23}$ is an alkylene group containing 1–6 carbon atoms, or an arylene group containing 6–12 carbon atoms, and Z$^2$ is the oxygen atom or NH; $A^2$ is a divalent group derived from an ethylenic unsaturated monomer copolymerizable with monomers forming other unit portions; and $x^2$ and $y^2$ both representing molar percents range from 50 to 99, and from 1 to 50, respectively, and $z^2$ represents the remaining molar percent including O.

The medium for electrophoresis of the present invention has improved precessiblility as well as high resolving power. For example, a process of cutting the medium with a edged tool such as dividing an obtained oblong polyacrylamid gel into the mediums or making a sample slot at the end of the medium, is easily and surely performed without destruction of the medium or deformation of the cut face. Thus the medium for electrophoresis of the present invention can be prepared in a mass scale.

When the medium is prepared on a plastic material support, the process of the preparation would become more easy and the medium can be handled, preserved, transported, etc. more easily. For above reasons, the medium for electrophoresis of the invention is especially advantageous for the system of preparing a polyacrylamide gel membrane (the medium for electrophoresis) in a mass scale and supplying technicians of electrophoresis with it at their requests.

DETAILED DESCRIPTION OF THE INVENTION

The medium for electrophoresis of the invention can be prepared on a support, and is generally preserved, transported and handled on the support. However the support used in the preparation of the medium may be replaced with other material before the medium is preserved, transported or handled.

Examples of the support employable for the preparation of the medium for electrophoresis of the present invention include a variety of waterproof materials in the form of sheet (the term "sheet" includes a film and a plate), such as glass plate, polymer coated paper, a plastic material. However, a plastic material sheet is advantageously used for the medium for electrophoresis of the present invention.

Examples of the support of the plastic material sheet employable for the medium for electrophoresis include a variety of polymer materials in the form of sheet. Examples of the polymer materials include polyethylene terephthalate, polycarbonate of Bisphenol A, polyvinyl chloride, vinylidene chloride-vinyl chloride copolymer, polymethyl methacrylate, polyethylene, polypropylene, cellulose acetates, and cellulose acetate propionate. Preferred is a polyethylene terephthalate sheet.

The medium for electrophoresis is now described in more detail.

The medium for electrophoresis (may be preferred to herein as "gel membrane") of this invention is consisting essentially of an aqueous polyacrylamide gel formed by crosslinking polymerization of an acrylamide compound and an acrylamide copolymer having at least one specifically selected constitutional repeating unit in the presence of water.

For the preparation of the polyacrylamide gel membrane, the acrylamide compound and the acrylamide copolymer are dissolved or dispersed in water to prepare an aqueous solution or an aqueous dispersion, in which the crosslinking reaction is carried out to form the aqueous polyacrylamide gel membrane. Hereinafter, the term "dissolving (in water)" means to include both "dissolving (in water)" and "dispersing (in water)", and the term "aqueous solution" means to include both "aqueous solution" and "aqueous dispersion", unless otherwise indicated. The term "aqueous medium" is used to include both a simple water as well as an aqueous mixture of water and an organic solvent, the organic solvent being optionally added.

Examples of the monofunctional acrylamide compound employable in the present invention include acrylamide and its homologues such as N-methylacrylamide, N,N-dimethylacrylamide, N-(hydroxymethyl)acrylamide and diacetonacrylamide, as well as methacrylamide and its homologues. These compounds can be employed independently or in combination. Acrylamide is most preferred among these acrylamide compounds, and said acrylamide can be also preferably employed in combination with one or more of other acrylamide compounds.

The acrylamide copolymer employed in the invention has at least one constitutional repeating unit selected from the group consisting of the following repeating units (1) and (2).

(1) A repeating unit having the formula (1):

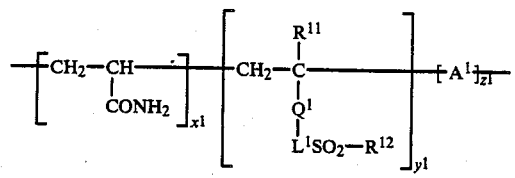

in which $R^{11}$ is the hydrogen atom or an alkyl group containing 1-6 carbon atoms; $Q^1$ is —COO—, —CON($R^{11}$)—, or an arylene group containing 6-10 carbon atoms; $L^1$ is a divalent group containing at least one linkage selected from the group consisting of —COO— and —CON($R^{11}$)— and containing 3-15 carbon atoms, or a divalent group containing at least one linkage selected from the group consisting of —O—, —N($R^{11}$)—, —CO—, —SO—, —SO$_2$—, —SO$_3$—, —SO$_2$N($R^{11}$)—, —N($R^{11}$)CON($R^{11}$)— and —N($R^{11}$)COO—, and containing 1-12 carbon atoms, in which $R^{11}$ has the same meaning as defined above; $R^{12}$ is —CH=CH$_2$ or —CH$_2$CH$_2$X$^1$, in which X$^1$ is a substituent replaceable with a nucleophilic group or releasable in the form of HX$^1$ by a base; A$^1$ is a divalent group derived from an ethylenic unsaturated monomer copolymerizable with monomers forming other unit portions (shown in the left therefrom); and x$^1$ and y$^1$ both representing molar percents range from 50 to 99, and from 1 to 50, respectively, and z$^1$ represents the remaining molar percent including 0;

Examples of $R^{11}$ in the above formula (1) include methyl, ethyl, butyl and n-hexyl groups.

Examples of $Q^1$ include

—COO—, —CONH—, —CON(CH$_3$)—, —CON(C$_2$H$_5$)—,

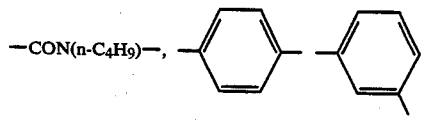

Examples of $L^1$ include the following divalent groups, which can be arranged in any direction within the formula (1), so far as it can connect $Q^1$ and SO$_2$:

—CH$_2$COOCH$_2$—, —CH$_2$COOCH$_2$CH$_2$—,
 —CH$_2$CH$_2$COOCH$_2$—, —(CH$_2$)$_5$COOCH$_2$CH$_2$—,
 —(CH$_2$)$_{10}$COOCH$_2$CH$_2$—, —CH$_2$NHCOCH$_2$—,
—CH$_2$NHCOCH$_2$CH$_2$—, —(CH$_2$)$_3$NHCOCH$_2$CH$_2$—,
—(CH$_2$)$_5$NHCOCH$_2$CH$_2$—, —(CH$_2$)$_{10}$NHCOCH$_2$CH$_2$—,
—CH$_2$OCH$_2$—, —CH$_2$CH$_2$OCH$_2$CH$_2$CH$_2$—,
—N(CH$_3$)CH$_2$CH$_2$—, —CH$_2$N(CH$_3$)CH$_2$CH$_2$—
—COCH$_2$CH$_2$—, —CH$_2$COCH$_2$CH$_2$—,

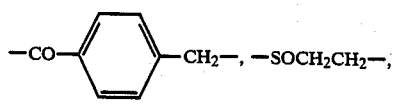

—CH$_2$SOCH$_2$CH$_2$—, —SO$_2$CH$_2$CH$_2$—,
—SO$_2$CH$_2$CH$_2$SO$_2$CH$_2$CH$_2$—,
—SO$_2$CH$_2$CH$_2$SO$_2$CH$_2$CH(OH)CH$_2$—, —SO$_3$CH$_2$CH$_2$CH$_2$—,
—SO$_3$CH$_2$COOCH$_2$CH$_2$—, —SO$_3$CH$_2$CH$_2$COOCH$_2$CH$_2$—,
—SO$_2$NHCH$_2$COOCH$_2$CH$_2$—,
—SO$_2$NHCH$_2$CH$_2$COOCH$_2$CH$_2$—, —NHCONHCH$_2$CH$_2$—,
—CH$_2$NHCONHCH$_2$CH$_2$—, —NHCOOCH$_2$CH$_2$—, and
 CH$_2$NHCOOCH$_2$CH$_2$—.

$R^{12}$ is —CH=CH$_2$ or —CH$_2$CH$_2$X$^1$. Examples of X$^1$ include:

halogen atoms such as chlorine and bromine;
hydroxyl group;
alkylsulfonyloxy groups such as methylsulfonyloxy (H$_3$CSO$_3$—), ethylsulfonyloxy, and propylsulfonyloxy;
arylsulfonyloxy groups such as phenylsulfonyloxy

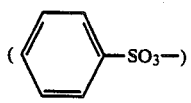

and p-tolylsulfonyloxy; and
alkylcarbonyloxy groups such as acetoxy, propionyloxy, trifluoromethylcarbonyloxy and dichloromethylcarbonyloxy. Accordingly, examples of $R^{12}$ include the following groups:

—CH=CH$_2$, —CH$_2$CH$_2$Cl, —CH$_2$CH$_2$Br, —CH$_2$CH$_2$O$_3$SCH$_3$,

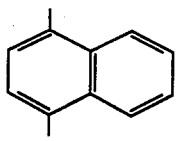

—CH$_2$CH$_2$OH, —CH$_2$CH$_2$OOCCH$_3$, —CH$_2$CH$_2$OOCCF$_3$, and
 —CH$_2$CH$_2$OOCCHCl$_2$.

Examples of the divalent group represented by A$^1$ include groups derived from the following ethylenic unsaturated monomers: ethylene, propylene, 1-butene, isobutene, styrene, chloromethylstyrene, hydroxymethylstyrene, sodium vinylbenzenesulfonate, sodium vinylbenzylsulfonate, N,N,N-trimethyl-N-vinylbenzylammonium chloride, N,N-dimethyl-N-benzyl-N-vinylbenzylammonium chloride, α-methylstyrene, vinyltoluene, 4-vinylpyridine, 2-vinylpyridine, benzylvinylpyridinium chloride, N-vinylacetamide, N-vinylpyrrolidone, 1-vinyl-2-methylimidazole, mono-ethylenic unsaturated esters of aliphatic carboxylic acid (e.g., vinyl acetate and allyl acetate), ethylenic unsaturated monocarboxylic acids or dicarboxylic acids and salts thereof (e.g., acrylic acid, methacylic acid, itaconic acid, maleic acid, sodium acrylate, potassium acrylate, sodium methacrylate), maleic anhydride, esters of ethylenic unsaturated monocarboxylic acids or dicarboxylic acids (e.g., n-butyl acrylate, n-hexyl acrylate, hydrdoxyethyl acrylate, cyanoethyl acrylate, (diethylamino)ethyl acrylate, methyl methacrylate, n-butyl methacrylate, benzyl methacrylate, hydroxyethyl methacrylate, chloroethyl methacrylate, methoxyethyl methacrylate, (diethylamino)ethyl methacrylate, N,N,N-triethyl-N-methacryloyloxyethylammonium p-toluenesulfonate, N,N-diethyl-N-methyl-N-methacryloyloxyethylammonium p-toluenesulfonate, dimethyl itaconate, and monobenzyl maleate), amides of ethylenic unsaturated monocarboxylic acid or dicarboxylic acid (e.g., N,N-dimethylacrylamide, N-methylolacrylamide, and N-

[(dimethylamino)propyl]acrylamide), N,N,N-trimethyl-N-(acryloylpropyl)ammonium p-toluenesulfonate, sodium 2-acrylamide-2-methylpropanesulfonate, acryloylmorpholine, methacrylamide, N,N-dimethyl-N'-acryloylpropanediamine propionate betaine, and N,N-dimethyl-N'-methacryloylpropanediamine acetate betaine.

In the case that the acrylamide copolymer of the invention is employed in the form of a crosslinked latex, $A^1$ can be other groups derived monomers containing at least two copolymerizable ethylenic unsaturated groups (e.g., divinyl benzene, methylenebisacrylamide, ethyleneglycol diacrylate, trimethylene glycol diacrylate, ethyleneglycol dimethacrylate, trimethylene glycol dimethacrylate, neopentylglycol dimethacrylate, etc.).

(2) A repeating unit having the formula (2):

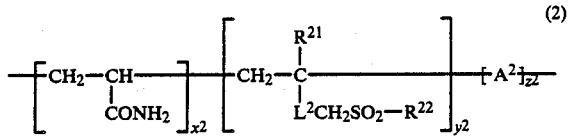

in which $R^{21}$ is the hydrogen atom or an alkyl group containing 1–6 carbon atoms; $R^{22}$ is $-CH=CH_2$ or $-CH_2CH_2X^2$, in which $X^2$ is a substituent replaceable with a nucleophilic group or releasable in the form of $HX^2$ by a base; $L^2$ is a divalent group selected from the group consisting of an alkylene group containing 1–6 carbon atoms (e.g., methylene, ethylene, and isobutylene), an arylene group containing 6–12 carbon atoms (e.g., phenylene, tolylene, and naphthalene), $-COZ^2-$, and $-COZ^2R^{23}-$, in which $R^{23}$ is an alkylene group containing 1–6 carbon atoms, or an arylene group containing 6–12 carbon atoms, and $Z^2$ is the oxygen atom or NH; $A^2$ is a divalent group derived from an ethylenic unsaturated monomer copolymerizable with monomers forming other unit portions; and $x^2$ and $y^2$ both representing molar percents range from 50 to 99, and from 1 to 50, respectively, and $z^2$ represents the remaining molar percent including O.

In the formula (2), examples of $R^{21}$, $R^{22}$ and $A^2$ include the respective groups listed for $R^{11}$, $R^{12}$ and $A^1$ of the formula (1).

Processes for syntheses of representative ethylenic unsaturated monomers containing a vinylsulfonyl groups or a functional group convertible into a vinylsulfonyl group which are employable for the preparation of the polymers comprising the repeating unit represented by the formula (1) or (2) are illustrated below.

SYNTHESIS EXAMPLE 1

Synthesis of N-[3-(2-chloroethylsulfonyl)propanamidomethyl]acrylamide

In a 2-l reaction vessel, 1,400 ml of distilled water, 244 g. of sodium sulfite and 220 g. of sodium hydrogencarbonate were stirred to give a solution. To the resulting solution chilled with ice-water to maintain the temperature at approx. 5° C. was dropwise added for 1.5 hours 260 g. of chloroethanesulfonyl chloride. To the resulting mixture was further added dropwise for approx. 15 min. 160 g. of 49% sulfuric acid. The mixture was then stirred at 5° C. for 1 hour, and the produced crystalline precipitate was filtered off. The precipitate was then washed with 400 ml of distilled water. The filtrate and the water collected from the washing were together introduced into a 3-l reaction vessel. Into the reaction vessel chilled with ice to maintain the temperature at approx. 5° C. was dropwise added for 30 min. a solution of 246 g. of methylenebisacrylamide in a mixture of 480 ml of distilled water and 1,480 ml of ethanol. The reaction vessel was then stored in a refrigerator for 5 days to complete the reaction. The precipitated crystals were collected by filtration and washed with 800 ml of chilled distilled water. The crystals were then recrystallized from 2,000 ml of 50% aqueous ethanol to give 219 g. of the desired monomer: yield 49%.

Among the acrylamide copolymers employed in this invention, copolymers comprising the following repeating unit are preferred.

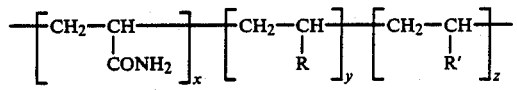

In the above formula, x, y and z mean molar percents for respective groups, and R and R' mean the following substitutents.

P-1  $x = 92$,  $y = 8$,  $z = 0$,  $R = -COOCH_2CH_2OCOCH_2CH_2SO_2CH=CH_2$

P-2  $x = 90$,  $y = 10$,  $z = 0$,  $R = -CONHCH_2NHCOCH_2CH_2SO_2CH=CH_2$

P-3  $x = 80$,  $y = 8$,  $z = 12$,  $R = -CONHCH_2NHCOCH_2CH_2SO_2CH=CH_2$ $R' = -CONH_2C(CH_3)_2CH_2COCCH_3$

P-4  $x = 92$,  $y = 8$,  $z = 0$,  $R = $ 

P-5  $x = 92$,  $y = 8$,  $z = 0$,  $R = $ 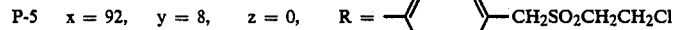

P-6   x = 92,   y = 8,   z = 0,    R = —CONHCH$_2$CH$_2$CH$_2$COON 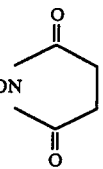

P-7   x = 92,   y = 8,   z = 0,    R = —CONHCH$_2$NHCOCH$_2$CH$_2$SO$_2$CH$_2$CH$_2$Cl
P-8   x = 80,   y = 8,   z = 12,   R = —CONHCH$_2$NHCOCH$_2$CH$_2$SO$_2$CH$_2$CH$_2$Cl
                                   R' = —CONH$_2$C(CH$_3$)$_2$CH$_2$COCH$_3$

P-9   x = 80,   y = 8,   z = 12,   R = 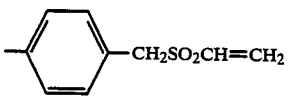—CH$_2$SO$_2$CH=CH$_2$

R' = —CONHCH$_2$OH

P-10  x = 80,   y = 8,   z = 12,   R = 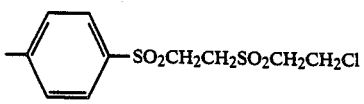—SO$_2$CH$_2$CH$_2$SO$_2$CH$_2$CH$_2$Cl R' = —CON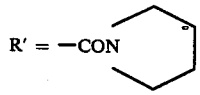

P-11  x = 80,   y = 8,   z = 12,   R = 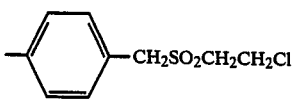—CH$_2$SO$_2$CH$_2$CH$_2$Cl

R' = —CON(CH$_3$)$_2$
P-12  x = 92,   y = 8,   z = 0,    R = —COOCH$_2$CH$_2$OCOCH$_2$SO$_2$CH=CH$_2$

Processes for the synthesis of the preferable copolymers represented by P-2 and P-8 are illustrated below.

SYNTHESIS EXAMPLE 2

Synthesis of copolymer of N-{[3-(vinylsulfonyl)propanamido]methyl}acrylamide and acrylamide (corresponding to P-2)

In a 200-ml reaction vessel, 5.65 g. of the monomer of the synthesis example 1, 12.8 g. of acrylamide, and 80 ml of 50% aqueous methanol were heated to 60° C. under stirring. To the resulting mixture was added 0.1 g. of 2,2'-azobis(2,4-dimethylvaleronitrile) and after 30 min. further added 0.1 g. of the same reagent. The mixture was then heated under stirring for 1 hour, and chilled with ice-water to approx. 10° C. To the chilled mixture was added a solution of 2.5 g. of triethylamine in 80 ml of methanol, and the mixture was further stirred. The mixture was then added under stirring to 1 l of acetone. The produced precipitate was collected by filtration to give 15.9 g. of the desired polymer: yield 90%.

The sulfonyl content of thus obtained polymer was $0.95 \times 10^{-3}$ eq./g.

SYNTHESIS EXAMPLE 3

Synthesis of copolymer of N-{[3-(2-chloroethylsulfonyl)propanamido]methyl}acrylamide, acrylamide and N-(1,1-dimethyl-2-oxobutyl)acrylamide (corresponding to P-8)

In a 500-ml reaction vessel, 10.3 g. of the monomer of the synthesis example 1, 29.2 g. of acrylamide, 11.3 g. of N-(1,1-dimethyl-2-oxobutyl)acrylamide, and 160 ml of 50% aqueous methanol were heated to 60° C. under stirring. To the resulting mixture was added 0.2 g. of 2,2'-azobis(2,4-dimethylvaleronitrile) and after 30 min. further added 0.2 g. of the same reagent. The mixture was then heated under stirring for 1 hour. This was introduced into a cellulose tube and subjected to dialysis for 2 days. The remaining solid was freeze-dried to give 43.2 g. of the desired white polymer: yield 85%.

The chlorosulfonyl content of thus obtained polymer was $0.8 \times 10^{-3}$ eq./g.

The acrylamide copolymer preferably employable in the invention has a molecular weight in the range of approx. 10,000 to approx. 1,000,000.

The acrylamide copolymer can be employed in an amount of approx. 1 to 50 wt.%, preferably approx. 5 to 40 wt.%, based on the total weight of the monomer (i.e., acrylamide compound).

The polyfunctional crosslinking agent is optionally employed to obtain the polyacrylamide gel membrane in this invention. A known crosslinking agent described, for instance, in "Electrophoresis" 1981, 2, 213–228 can be employed singly or in combination. Examples of the crosslinking agent include bifunctional compounds such as N,N'-methylenebisacrylamide (BIS), N,N'-propylenebisacrylamide (PBA), di(acrylamide dimethyl)ether (i.e., N,N'-oxydimethyleneacrylamide), 1,2-diacrylamide ethyleneglycol (DEG), 1,3-diacryloylethyleneurea, ethylene diacrylate (EDA), N,N'-diallyltartardiamide (DATD) and N,N'-bisacrylylcystamine (BAC), and trifunctional compounds such as 1,3,5-triacryloylhexahydro-s-triazin, triallylcyanurate and triallylisocyanurate.

The crosslinking agent can be employed in an amount of not more than approx. 30 wt.%, preferably not more than approx. 10 wt.%, based on the total weight of acrylamide compound, acrylamide copolymer and the crosslinking agent.

The gel concentration preferably is in the range of approx. 3 to 30 wt/v % [total weight of acrylamide compound and acrylamide copolymer (and optionally added crosslinking agent) per total volume of gel membrane comprising acrylamide compound, acrylamide copolymer and water (and optionally added crosslinking agent)], the concentration being expressed in accordance with the diffinition indicated by S. Hjerten in Arch. Biochem. Biophys. 1 (Suppl.), 147 (1962).

The medium for electrophoresis of the invention can be employed for analysis of proteins and conjugated proteins (e.g., lipoproteins, glycoproteins, etc.) and the medium (gel membrane) of the element may comprise an anionic surfactant as a modifier. The use of the anionic surfactant is generally essential or preferable for the electrophoretic analyses of proteins or conjugated proteins, because it favorably contributes to perform separation of the protein and conjugated protein and determination of molecular weight of these proteins. However, the medium for electrophoresis may not contain the anionic surfactant.

Examples of the anionic surfactant include alkylsulfates, particularly alkylsulfates having a long chain alkyl group of at least 10 carbon atoms. The cation contained for formation of the salt generally is an alkali metal ion such as sodium ion, potassium ion, or lithium ion. Sodium ion is preferred from the economical viewpoint. The alkylsulfates preferably are dodecylsulfates (salts of sodium, potassium, lithium, etc.), and particularly preferred is sodium dodecylsulfate (SDS). The introduction of SDS into the gel membrane is particularly advantageous for separation of proteins and conjugated proteins, as well as for determination of molecular weight thereof. The anionic surfactant (modifier) can be contained in the gel-forming solution in an amount of approx. 0.05 to 2.0 wt/v % (weight per volume of the gel forming solution), preferably approx. 0.1 to 1.5 wt/v %.

The medium for electrophoresis of the invention also can be employed for determination of base sequence of DNA, RNA, their fragments, and their derivatives. For this purpose, a compound containing at least one carbamoyl group is generally incorporated into the electrophoresis medium as a modifier. Examples of the modifier include urea and formamide. Urea is most preferred. The modifier can be used in an amount of approx. 40 to 60 wt.% based on the volume of the aqueous gel. In the case that urea is used as the modifier, the amount generally ranges from approx. 6 moles (approx. 360 g.) per one liter of the aqueous gel to the saturation amount, preferably from approx. 7 moles (approx. 420 g.) to the saturation amount.

The gel membrane of the invention may contain a water-soluble polymer. As the water-soluble polymer, a water-soluble polymer of the addition polymerization type or condensation polymerization type can be used. Examples of the polymer of the addition polymerization type include non-ionic water-soluble polymers such as polyvinyl alcohol, polyvinyl pyrrolidone, and polyacrylamide. Examples of polymer of the condensation polymerization type include non-ionic water-soluble polyalkylene glycols such as polyethylene glycol and polypropylene glycol. The water-soluble polymer of molecular weight ranging from approx. 10,000 to 1,000,000 is preferably used. Among these water-soluble polymers, polyacrylamide and polyethylene glycol are preferable. The water-soluble polymer is used in the range of approx. 2 to 100 wt.%, preferably, approx. 5 to 50 wt.%, based on the total weight of the monomer and crosslinking agent.

The addition of a water-soluble polymer serves to impart elasticity to the gel membrane, and thus modified gel membrane is still elastic even even if it is dried. Thus, the gel membrane is so improved as to be free from brittleness, whereby the gel membrane becomes hardly breakable. Further, the viscosity of the gel membrane can be controlled by selecting the molecular weight and amount of the water-soluble polymer.

The gel membrane preferably contains agarose. There is no specific limitation on the agarose to be contained in the gel membrane, and any type of agarose such as low-electroendosmosis agarose, medium-electroendosmosis agarose, or high-electroendosmosis agarose can be used. Examples of agarose employable in the invention include agaroses disclosed in Japanese Patent Provisional Publication Nos. 55(1980)-5730, 55(1980)-110946 (corresponding to U.S. Pat. No. 4,290,911 and GB No. 2 042 571A), 57(1982)-502098 (WO No. 82/02599, U.S. Pat. No. 4,319,976), etc. The amount of agarose to be added ranges from approx. 0.2 to 2 wt/v %, preferably from approx. 0.3 to 1.2 wt/v %, based on the volume of the aqueous gel containing the monomer and crosslinking agent. It becomes possible by the addition of agarose that the viscosity of the gel forming solution can be controlled through changing the temperature of the solution, whereby suppressing flowability of the solution as well as facilitating the formation of the gel membrane.

A pH buffer agent can be contained in the gel membrane of the invention.

In the medium for electrophoresis of protein and protein derivatives, a buffer agent which is able to buffer a solution to a range of pH 2.5 to 10.0 can be incorporated. Such buffer agent are described in publications such as "Chemistry Handbook, Fundamental Edition" compiled by The Chemical Society of Japan (Maruzen Ltd., Tokyo, 1966) pages 1312—1320; "Modern Electrophoresis" edited by Aoki & Nagai (Hirokawa Shoten, 1973), pages 320–322; "Data for Biochemical Research" compiled by R. M. C. Dawson et al., second edition (Oxford at the Clarendon Press, 1969) pages 476–508; "Biochemistry" 5, 467 (1966); and "Analytical Biochemistry" 104, pages 300–310 (1966). Examples of the buffer agent include a buffer agent containing barbital, a buffer agent containing tris(hydroxymethyl)aminomethane (Tris), a buffer agent containing phosphate, a buffer agent containing borate, a buffer agent containing acetic acid or acetate, a buffer agent containing citric acid or citrate, a buffer agent containing lactic acid or lactate, and a buffer containing glycine; as well as N,N-bis(2-hydroxyethyl)glycine (Bicine), N-2-hydroxyethyl)glycine (Bicine), N-2-hydroxyethylpiperazine-N'-2-hydroxypropane-3-sulfonic acid (HEPPSO) or its salt, N-2-hydroxyethylpiperazine-N'-3-propanesulfonic acid (EPPS) or its salt, N-[tris(hydroxymethyl)methyl]-3-aminopropanesulfonic acid (TAPS) or its salt. Preferable examples of the buffer agent include potassium dihydrogenphosphate-disodium hydrogenphosphate, Tris-sodium borate, Tris-sodium borate-EDTA.2Na, Tris-citric acid, sodium barbital-sodium acetate, sodium barbital-hydrochloric acid, barbital-sodium barbital, acetic acid-sodium acetate, lactic acid-sodium lactate, citric acid-disodium hydrogenphosphate, Bicine, HEPPSO, sodium salt of HEPPSO, EPPS, sodium salt of EPPS, TAPS, sodium salt of TAPS, etc.

In the medium for electrophoresis of DNA and the like, a buffer agent which is able to buffer a solution to a range of pH 8.0 to 9.0, preferably pH 8.2 to 8.3 can be incorporated. Such buffer agents are described in the aforementioned publications.

Examples of the buffer agent include tri(hydroxymethyl)aminomethane (Tris), N,N-bis(2-hydroxyethyl)glycine (Bicine), N-2-hydroxyethylpiperazine-N'-2-hydroxypropane-2-sulfonic acid or its Na or K salt, N-2-hydroxyethylpiperazine-N'-2-hydroxypropane-3-sulfonic acid (HEPPSO) or its Na or K salt, N-[tris(hydroxymethyl)methyl]-3-aminopropanesulfonic acid (TAPS) or its Na or K salt; as well as an acid, an alkali, and a salt employable in combination with the compounds. Preferable examples of the buffer agent include Tris, boric acid-EDTA.2Na (pH 8.3).

A polyol compound such as glycerol or ethylene glycol can be contained in the aqueous gel membrane of the invention as a wetting agent. The polyol compound can be introduced in an amount of approx. 5 to 40 wt.% based on the volume of the aqueous gel membrane. Glycerol is particularly preferable among the polyol compounds. The addition of the wetting agent serves to keep the gel membrane from excessive dryness possibly caused by evaporation of water during storage of the medium, whereby preventing the medium from turning brittle or cracking caused by the excessive dryness. Thus, the improvement of physical properties of the gel membrane is accomplished.

The gel membrane of the invention may contain an oxidation inhibitor. The oxidation inhibitor can be chosen from various compounds heretofore known as oxidation inhibitors employable for the gel membrane for electrophoresis. Examples of the oxidation inhibitor include 1,4-dithiothreitol and 2-mercaptoethanol.

A representative medium for electrophoresis of this invention (the polyacrylamide gel membrane) is formed by radical crosslinking polymerization between the monomer (i.e., acrylamide compound) and the acrylamide copolymer in an aqueous medium in which the water-soluble polymer and agarose etc. are dissolved almost homogeneously. Thus obtained gel is assumed to have a structure in which the water-soluble polymer and agarose are dispersed in the three dimensional crosslinking polymer formed by the reaction of the acrylamide compound and the acrylamide copolymer, and the water-soluble polymer and agarose are further entangled with the three dimensional crosslinked polymer structure.

The crosslinking polymerization can be initiated by a known method, for instance, in the presence of a peroxide and/or under irradiation of ultraviolet rays. The reaction can be further accelerated by heat and irradiation with ultraviolet rays.

As the polymerization catalyst, a known low temperature-polymerization initiator such as those described in "Electrophoresis" 1981, 2, 213-219, ibid. 1981, 2, 220-228; and "Modern Electrophoresis" edited by Aoki & Nagai (Hirokawa Shoten, 1973) can be used. Examples of the initiator include a mixture of β-dimethylaminopropionitrile (DMAP) and ammonium peroxodisulfate, a mixture of N,N,N',N'-tetramethylethylenediamine (TEMED) and ammonium peroxodisulfate, a mixture of TEMED and riboflavin, a combination of a mixture of TEMED, riboflavin and hydrogen peroxide, and irradiation with ultraviolet rays. The radical reaction initiator can be employed in the amount of approx. 0.3 to 5 wt. %, preferably approx. 0.5 to 3 wt. %, based on the total amount of the acrylamide compound and acrylamide copolymer (and optionally added crosslinking agent).

In the case that the medium for electrophoresis of this invention is formed on a support as a membrane or layer, it can be prepared by a process in which a gel-forming solution is coated by a known method on a support having a smooth surface, and the gel forming solution is crosslinked to polymerization thereon. Preferably the gel-forming solution is coated on a support on which an adhesive layer such as a layer containing a cellulose derivative is preliminarily provided to improve the adhesion between the medium for electrophoresis and the support. When a plastic material supprot is used, the provision of the adhesive layer is especially advantageous.

In the case that the gel-forming solution is crosslinked to polymerization on the surface of the support, the surface of the gel-forming solution can be covered with a cover film, sheet, or plate. The same material as employable for the support can be employed as the cover film, sheet, and plate. The cover film has generally thickness of not more than 300 μm, preferably from approx. 4 μm to approx. 200 μm. The cover film may be removed in the autoradiographic process.

In the case that the covering material is thick (e.g., approx. 70 to 300 μm), the medium for electrophoresis of the present invention can be prepared by the following steps: the gel forming solution is first coated on the covering material and crosslinked thereon to form the desired gel medium layer, and then a support is provided on the gel medium layer.

The gel membrane of the invention can be employed for the horizontal or vertical electrophoresis, disc electrophoresis, etc. by known methods described, for instance, in the aforementioned texts.

The present invention will be more clearly understood with reference to the following examples.

EXAMPLE 1

A surface of a polyethylene terephthalate sheet (thickness 180 μm) was made hydrophilic. On the surface of the sheet (support) was coated a gel forming solution containing the components set forth in Table 1 to have a thickness of approx. 300 μm. The polyacrylamide gel membrane was obtained by crosslinking polymerization of the coated solution in a nitrogen atmosphere. A slot for sample inlet was formed at the end of the gel membrane using a cutter. Then the surface of the gel membrane was covered with a polyethylene terephthalate sheet (cover film; thickness 100 μm) having hydrophilic surface to obtain a element for electrophoresis.

TABLE 1

| Sample No. | 1 | 2 | 3 | 4 |
|---|---|---|---|---|
| Acrylamide (g.) | 9.85 | 8.96 | 8.69 | 8.96 |
| P-2 (g.) | — | 1.0 | 3.0 | — |
| P-8 (g.) | — | — | — | 1.0 |
| BIS (g.) | 0.15 | 0.14 | 0.11 | 0.14 |
| SDS (g.) | 0.10 | 0.10 | 0.10 | 0.10 |
| Agarose (ml) | 15.0 | 15.0 | 15.0 | 15.0 |
| Disodium Hydrogen phosphate 12 Hydrate (g.) | 3.58 | 3.58 | 3.58 | 3.58 |

TABLE 1-continued

| Sample No. | 1 | 2 | 3 | 4 |
|---|---|---|---|---|
| Sodium Dihydrogen phosphate 12 Hydrate (g.) | 0.33 | 0.33 | 0.33 | 0.33 |
| Water added to make | 100 ml | 100 ml | 100 ml | 100 ml |
| TEMED (μl) | 33 | 33 | 33 | 33 |
| APS (ml) | 1.3 | 1.3 | 1.3 | 1.3 |

Remarks:
P-2; N—{[3-(vinylsulfonyl)propanamido]methyl}acrylamide.acrylamide. copolymer,
P-8; N—{[3-(2-chloroethylsulfonyl)propanamido]methyl}acrylamide.acrylamide.-N-(1,1-dimethyl-2-oxobutyl)acrylamide.copolymer,
BIS; N,N'—methylenebis acrylamide (bifunctional crosslinking agent),
SDS; Sodium dodecylsulfate,
Agarose; (2 wt. % in aqueous solution, low-electroendosmosis, gelling temperature 36° C.),
TEMED; N,N,N',N'—tetramethylethylenediamine (5 wt. % in aqueous solution),
APS; Ammonium peroxodisulfate (5 wt. % in aqueous solution).

In Table 1, Sample No. 1 is a comparative sample, and Samples No. 2 to No. 4 are samples according to this invention. Both TEMED and APS are the polymerization initiators.

When the slot for sample inlet was formed, the gel of Sample No. 1 (comparative sample) clung to the cutter, so that a part of the gel membrane adjacent to the slot was distorted. On the contrary, the above process for Samples No. 2 to No. 4 (according to the invention) was easily and surely performed without above distortion.

A control (standard) protein was electrophoresed on the media for electrophoresis (the Samples No. 1 to No. 4). The media were then immersed in an aqueous Coomasie Blue R-250 (Colour Index Constitution Number 42660) solution (0.1%) for dyeing. As a result of examining the resolving property for the protein of each sample, it was observed that the resolved patterns on the polyacrylamide gel membranes according to this invention (Samples No. 2 to No. 4) had sharper bands than that on the comparative gel membrane (Sample No. 1).

EXAMPLE 2

On the surface of the sheet (support) was coated a gel forming solution containing the components set forth in Table 2 to obtain a medium for electrophoresis in the same manner as in Example 1.

TABLE 2

| Sample No. | 5 | 6 | 7 | 8 |
|---|---|---|---|---|
| Acrylamide (g.) | 9.85 | 8.96 | 8.69 | 8.96 |
| P-2 (g.) | — | 1.0 | — | 1.0 |
| P-8 (g.) | — | — | 1.0 | 1.0 |
| TAHT | 0.15 | 0.14 | 0.11 | — |
| SDS (g.) | 0.10 | 0.10 | 0.10 | 0.10 |
| PAA (g.) | 1.0 | 1.0 | 1.0 | 1.0 |
| Agarose (ml) | 15.0 | 15.0 | 15.0 | 15.0 |
| Disodium Hydrogen phosphate 12 Hydrate (g.) | 3.58 | 3.58 | 3.58 | 3.58 |
| Sodium Dihydrogen phosphate 12 Hydrate (g.) | 0.33 | 0.33 | 0.33 | 0.33 |
| Water added to make | 100 ml | 100 ml | 100 ml | 100 ml |
| TEMED (μl) | 33 | 33 | 33 | 33 |
| APS (ml) | 1.3 | 1.3 | 1.3 | 1.3 |

Remarks:
TAHT; 1,3,5-triacryloylhexahydro-s-triazine (trifunctional crosslinking agent),
PAA; Polyacrylamide.

In Table 2, Sample No. 5 is a comparative sample, and Samples No. 6 to No. 8 are samples according to this invention. The other components represent the same meanings as in Table 1.

When the slot for sample inlet was formed, the gel of Sample No. 5 (comparative sample) clung to the cutter, so that a part of the gel membrane adjacent to the slot was distorted. On the contrary, the above process for Samples No. 6 and No. 7 (according to the invention) was easily and surely performed without above distortion. In the process for Sample No. 8 (according to the invention), a part of the gel membrane adjacent to the slot was slightly distorted, but it did not become a substantial problem.

A control (standard) protein was electrophoresed on the mediums for electrophoresis (the Samples No. 5 to No. 8). The mediums were then immersed in an aqueous Coomasie Blue R-250 (Colour Index Constitution Number 42660) solution (0.1%) for dyeing. As a result of examining the resolving property for the protein of each sample, it was observed that the resolved patterns on the polyacrylamide gel membranes according to this invention (Samples No. 6 to No. 8) had sharper bands than that on the comparative gel membrane (Sample No. 5). Especially the resolved patterns of Samples No. 6 and No. 7 had much more sharper bands.

EXAMPLE 3

A surface of two polyethylene terephthalate sheet were made hydrophilic by irradiation of ultraviolet rays. On the surface of one sheet (support) was formed a polyacrylamide gel membrane of 1 mm thick by coating a gel-forming solution containing 4.5 g. of acrylamide, 0.10 g. of 1,3,5-triacryloylhexahydro-s-triazine, 1.2 g. of N-{[3-(vinylsulfonyl)propanamido]methyl}acrylamide.acrylamide.copolymer (P-2), 0.6 g. of polyacrylamide, 0.3 g. of agarose (low-electroendosmosis, gelling temperature 36° C.), 1.08 g. of tris(hydroxymethyl)aminomethane [CAS Registry No. 77-86-1], 0.55 g. of boric acid, 93 mg. of EDTA.2Na salt and 20 g. of glycerol in 100 ml volume after addition of 1.3 ml of ammonium peroxodisulfate (5 weight %) and 33 μl of TEMED, both being the polymerization initiator, and causing the polymerization reaction. A slot for sample inlet was formed at the end of the gel membrane using a cutter. Then the surface of the gel membrane was covered with a polyethylene terephthalate sheet (cover film; thickness 100 μm) having hydrophilic surface to obtain a element for electrophoresis according to this invention.

On the surface of the other sheet (support) was formed a comparative polyacrylamide gel membrane of 1 mm thick by coating a gel-forming solution containing 5.73 g. of acrylamide, 0.13 g. of 1,3,5-triacryloylhexahydro-s-triazine, 0.6 g. of polyacrylamide, 0.3 g. of agarose (low-electroendosmosis, gelling temperature 36° C.), 1.08 g. of tris(hydroxymethyl)aminomethane, 0.55 g. of boric acid, 93 mg. of EDTA.2Na salt and 20 g. of glycerol in 100 ml volume after addition of 1.3 ml of ammonium peroxodisulfate (5 weight %) and 33 μl of TEMED, both being the polymerization initiator, and causing the polymerization reaction. A slot for sample inlet was formed at the end of the gel membrane using a cutter. Then the surface of the gel membrane was covered with a polyethylene terephthalate sheet (cover film; thickness 100 μm) having hydrophilic surface to obtain a comparative element for electrophoresis.

When the slot for sample inlet was formed, the gel of the comparative gel membrane clung to the cutter, so that a part of the gel membrane adjacent to the slot was largely distorted. On the contrary, the above process for the gel membrane according to the invention was easily and surely performed without above distortion.

Plasmid pBR-322 of *Escherichia coli* was treated by a restriction enzyme AsuI and then electrophoresed on the above mediums for electrophoresis. The mediums were then dyed with ethidium bromide. As a result of examining the resolving property for the DNA of each sample, it was observed that the resolved patterns on the polyacrylamide gel membranes according to the invention had sharper bands than that on the comparative gel membrane.

Therefore in an electrophoresis using the medium for electrophoresis according to the invention, identification and separation of the bands can be performed with ease and high accuracy.

EXAMPLE 4

On the surface of the sheet (support) was coated a gel forming solution containing the components set forth in Table 3 to obtain a medium for electrophoresis in the same manner as in Example 1.

TABLE 3

| Sample No. | 9 | 10 | 11 | 12 |
|---|---|---|---|---|
| Acrylamide (g.) | 11.99 | 10.81 | 8.50 | 10.81 |
| P-2 (g.) | — | 1.2 | 3.6 | — |
| P-8 (g.) | — | — | — | 1.2 |
| BIS (g.) | 0.21 | 0.19 | 0.15 | 0.19 |
| Urea (g.) | 42.0 | 42.0 | 42.0 | 42.0 |
| Agarose (ml) | 15.0 | 15.0 | 15.0 | 15.0 |
| Tris(hydroxymethyl) aminomethane (g.) | 1.08 | 1.08 | 1.08 | 1.08 |
| Boric acid (g.) | 0.55 | 0.55 | 0.55 | 0.55 |
| EDTA.2Na salt (g.) | 0.093 | 0.093 | 0.093 | 0.093 |
| Water added to make | 100 ml | 100 ml | 100 ml | 100 ml |
| TEMED (μl) | 33 | 33 | 33 | 33 |
| APS (ml) | 1.3 | 1.3 | 1.3 | 1.3 |

In Table 3, Sample No. 9 is a comparative sample, and Samples No. 10 to No. 12 are samples according to this invention. All of the components except Urea, Tris(hydroxymethyl)aminomethane, Boric acid and EDTA.2Na salt in Table 3 have the same meanings as in Table 1.

When the slot for sample inlet was formed, the gel of Sample No. 9 (comparative sample) clung to the cutter, so that a part of the gel membrane adjacent to the slot was distorted. On the contrary, the above process for Samples No. 10 to No. 12 (according to the invention) was easily and surely performed without above distortion.

A sample ($^{32}$P-DNA cleaved by Maxam-Gilbert method) was electrophoresed on the media for electrophoresis (the Samples No. 9 to No. 12). The mediums were subjected to the autoradiographic process for sequencing the DNA.

65 bases in base-sequence of the DNA were decoded by using the medium for electrophoresis accorging to the invention (Samples No. 9 to No. 12), while 45 bases were decoded by using the comparative medium (Sample No. 8).

EXAMPLE 5

On the surface of the sheet (support) was coated a gel forming solution containing the components set forth in Table 4 to obtain a medium for electrophoresis in the same manner as in Example 1.

TABLE 4

| Sample No. | 13 | 14 | 15 | 16 |
|---|---|---|---|---|
| Acrylamide (g.) | 11.91 | 10.81 | 8.50 | 10.81 |
| P-2 (g.) | — | 1.2 | 3.6 | 3.6 |
| TAHT (g.) | 0.23 | 0.19 | 0.15 | — |
| Urea (g.) | 42.0 | 42.0 | 42.0 | 42.0 |
| Agarose (ml) | 15.0 | 15.0 | 15.0 | 15.0 |
| PAA (g.) | 1.0 | 1.0 | 11.0 | 1.0 |
| Tris(hydroxymethyl) aminomethane (g.) | 1.08 | 1.08 | 1.08 | 1.08 |
| Boric acid (g.) | 0.55 | 0.55 | 0.55 | 0.55 |
| EDTA.2Na salt (g.) | 0.093 | 0.093 | 0.093 | 0.093 |
| Water added to make | 100 ml | 100 ml | 100 ml | 100 ml |
| TEMED (μl) | 33 | 33 | 33 | 33 |
| APS (ml) | 1.3 | 1.3 | 1.3 | 1.3 |

In Table 4, Sample No. 13 is a comparative sample, and Samples No. 14 to No. 16 are samples according to this invention. All of the components except Urea, Tris(hydroxymethyl)aminomethane, Boric acid and EDTA.2Na salt in Table 4 represent the same meanings as in Table 1 and Table 2.

When the slot for sample inlet was formed, the gel of Sample No. 13 (comparative sample) clung to the cutter, so that a part of the gel membrane adjacent to the slot was distorted. On the contrary, the above process for Samples No. 14 and No. 15 (according to the invention) was easily and surely performed without above distortion. In the process for Sample No. 16 (according to the invention), a part of the gel membrane adjacent to the slot was slightly distorted, but it did not become a substantial problem.

A sample (M-13.mp-11.SSDNA processed by Dideoxy method) was electrophoresed on the mediums for electrophoresis (the Samples No. 13 to No. 16). The media were subjected to the autoradiographic process for sequencing the DNA.

82 bases in base-sequence of the DNA were decoded by using the medium for electrophoresis accorging to the invention (Samples No. 14 to No. 16), while 53 bases were decoded by using the comparative medium (Sample No. 13).

I claim:

1. A medium for electrophoresis comprising an aqueous acrylamide gel formed by the reaction of an monofunctional acrylamide compound, an acrylamide copolymer and a polyfunctional cross-linking agent in the presence of water, wherein said acrylamide copolymer is employed in an amount of 1 to 50 wt. % based on the amount of said acrylamide compound, and said acrylamide copolymer has at least one set of repeating units selected from the group consisting of repeating units having the formula:

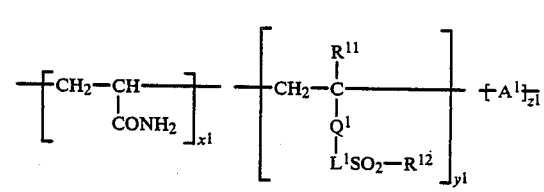

in which $R^{11}$ is the hydrogen atom or an alkyl group containing 1-6 carbon atoms; $Q^1$ is —COO—, —CON($R^{11}$)—, or an arylene hydrocarbon group of 6-10 carbon atoms; $L^1$ is a divalent group containing at least one linkage selected from the group consisting of —COO— and —CON($R^{11}$)— and containing 3-15 carbon atoms, or divalent group containing at least one linkage selected from the group consisting of —O—, —N($R^{11}$)—, —CO—, —SO—, —SO$_2$—, —SO$_3$—, —SO$_2$N($R^{11}$)—, —N($R^{11}$)CON($R^{11}$)— and —N($R^{11}$-

)COO⁻ and containing 1-12 carbon atoms, in which $R^{11}$ has the same meaning as defined above; $R^{12}$ is —CH=CH$_2$ or —CH$_2$CH$_2$X$^1$, in which X$^1$ is a substituent replaceable with a nucleophilic group or releasable in the form of HX$^1$ by a base; A$^1$ is a divalent group derived from an ethylenic unsaturated monomer copolymerizable with monomers forming other unit portions; and x$^1$ and y$^1$ both represent a molar percents range from 50 to 99, and from 1 to 50, respectively, and z$^1$ represents the remaining molar percent including O; and

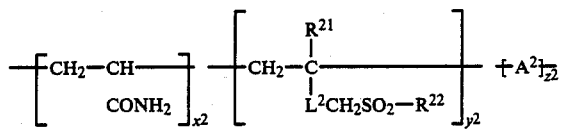

in which $R^{21}$ is the hydrogen atom or an alkyl group containing 1-6 carbon atoms; $R^{22}$ is —CH=CH$_2$ or —CH$_2$CH$_2$X$^2$, in which X$^2$ is a substituent replaceable with a nucleophilic group or releasable in the form of HX$^2$ by a base; L$^2$ is a divalent group selected from the group consisting of an alkylene group containing 1-6 carbon atoms, an arylene group containing 6-12 carbon atoms, —COZ$^2$—, and —COZ$^2$R$^{23}$—, in which $R^{23}$ is an alkylene group containing 1-6 carbon atoms, or an arylene group containing 6-12 carbon atoms, and Z$^2$ is the oxygen atom or NH; A$^2$ is a divalent group derived from an ethylenic unsaturated monomer copolymerizable with monomers forming other unit portions; and x$^2$ and y$^2$ both representing molar percents range from 50 to 99, and from 1 to 50, respectively, and z$^2$ represents the remaining molar percent including O.

2. The medium for electrophoresis as claimed in claim 1, in which said aqueous acrylamide gel is formed by crosslinking polymerization of said acrylamide compound and said acrylamide copolymer in the presence of water and a crosslinking agent selected from the group consisting of bifunctional compounds and trifunctional compounds.

3. The medium for electrophoresis as claimed in claim 1 or 2, in which a water-soluble polymer and agarose are contained.

4. The medium for electrophoresis as claimed in claim 1 or 2, in which an anionic surfactant is contained.

5. The medium for electrophoresis as claimed in claim 4, in which said anionic surfactant is an alkylsulfate.

6. The medium for electrophoresis as claimed in claim 5, in which said alkylsulfate is sodium dodecylsulfate.

7. The medium for electrophoresis as claimed in claim 1 or 2, in which a compound having at least one carbamoyl group is contained.

8. The medium for electrophoresis as claimed in claim 7 in which said compound having at least one carbamoyl group is urea or formamide.

9. The medium for electrophoresis as claimed in claim 1 or 2, in which said medium is provided on a plastic material support.

10. A medium for electrophoresis comprising an aqueous monofunctional acrylamide gel formed by the reaction of an acrylamide compound, an acrylamide copolymer and a polyfunctional cross-linking agent in the presence of water, wherein said acrylamide copolymer is employed in an amount of 1 to 50 wt. % based on the amount of said acrylamide compound, and said acrylamide copolymer has at least one set of repeating units selected from the group consisting of repeating units having the formula:

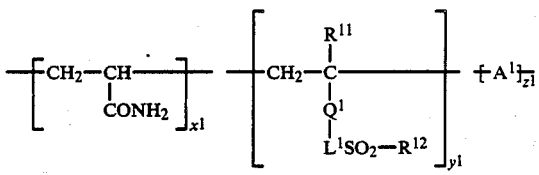

in which $R^{11}$ is the hydrogen atom or an alkyl group containing 1-6 carbon atoms; $Q^1$ is —COO—, —CON(R$^{11}$)—, or an arylene hydrocarbon group of 6-10 carbon atoms; L$^1$ is a divalent group containing at least one linkage selected from the group consisting of —COO— and —CON(R$^{11}$)— and containing 3-15 carbon atoms, or a divalent group containing at least one linkage selected from the group consisting of —O—, —N(R$^{11}$)—, —CO—, —SO—, —SO$_2$—, —SO$_3$—, —SO$_2$N(R$^{11}$)—, —N(R$^{11}$)CON(R$^{11}$)— and —N(R$^{11}$)COO⁻ and containing 1-12 carbon atoms, in which $R^{11}$ has the same meaning as defined above; $R^{12}$ is —CH=CH$_2$ or —CH$_2$CH$_2$X$^1$, in which X$^1$ is a substituent replaceable with a nucleophilic group or releasable in the form of HX$^1$ by a base; A$^1$ is a divalent group derived from an ethylenic unsaturated monomer copolymerizable with monomers forming other unit portions; and x$^1$ and y$^1$ both represent a molar percents range from 50 to 99, and from 1 to 50, respectively, and z$^1$ represents the remaining molar percent including O.

* * * * *